US011656355B2

(12) United States Patent
Lee

(10) Patent No.: US 11,656,355 B2
(45) Date of Patent: May 23, 2023

(54) DIRECT CHIP-ON-ARRAY FOR A MULTIDIMENSIONAL TRANSDUCER ARRAY

(71) Applicant: Siemens Medical Solutions USA, Inc., Malvern, PA (US)

(72) Inventor: Baik Woo Lee, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 505 days.

(21) Appl. No.: 16/947,018

(22) Filed: Jul. 15, 2020

(65) Prior Publication Data

US 2022/0018957 A1    Jan. 20, 2022

(51) Int. Cl.
*B06B 1/06* (2006.01)
*G01S 15/89* (2006.01)
*A61B 8/08* (2006.01)

(52) U.S. Cl.
CPC .......... *G01S 15/8993* (2013.01); *A61B 8/483* (2013.01); *B06B 1/06* (2013.01)

(58) Field of Classification Search
CPC ........ B06B 1/06; B06B 1/0607; B06B 1/0622
USPC ................................................. 310/322, 334
See application file for complete search history.

(56) References Cited

U.S. PATENT DOCUMENTS

| 7,304,415 | B2 | 12/2007 | Petersen et al. |
| 8,169,125 | B2 | 5/2012 | Savord |
| 8,207,652 | B2 * | 6/2012 | Baumgartner ....... A61B 8/4483 310/334 |
| 8,659,212 | B2 | 2/2014 | Eggen et al. |
| 8,754,574 | B2 | 6/2014 | Morris et al. |
| 9,180,490 | B2 | 11/2015 | Tai et al. |
| 2006/0116584 | A1 | 6/2006 | Sudol |
| 2008/0315724 | A1 * | 12/2008 | Kunkel, III ........... B06B 1/0633 310/334 |
| 2013/0315035 | A1 * | 11/2013 | Tai ...................... A61B 8/4494 367/140 |
| 2016/0271651 | A1 | 9/2016 | Petersen et al. |
| 2020/0009615 | A1 | 1/2020 | Lee |

OTHER PUBLICATIONS

Wildes, Douglas, et al. "4-D ICE: a 2-D array transducer with integrated ASIC in a 10-Fr catheter for real-time 3-D intracardiac echocardiography." IEEE transactions on ultrasonics, ferroelectrics, and frequency control 63.12 (2016) 2159-2173.

* cited by examiner

*Primary Examiner* — Derek J Rosenau

(57) ABSTRACT

For direct chip-on-array for a multi-dimensional transducer array, the generally rigid and conductive dematching layer is extended beyond a footprint of the transducer array. The ASIC is directly connected to the dematching layer on one side, while the other side provides for electrical connection to the elements of the array and I/O pads for connections (e.g., flex-to-dematching layer) to the ultrasound imaging system. By using the dematching layer rigidity, the ASIC may be protected during formation of the acoustic stack. By using the dematching layer conductivity, any mis-alignment is compensated by the routing through the dematching layer, and/or a large flat region is provided for I/O, allowing for good low temperature asperity contact connections with larger area than flip-chip solder bumps. By providing the I/O for the system connections on a different side of the dematching layer than the ASIC, a large keep-out distance due to underfill may be avoided.

20 Claims, 6 Drawing Sheets

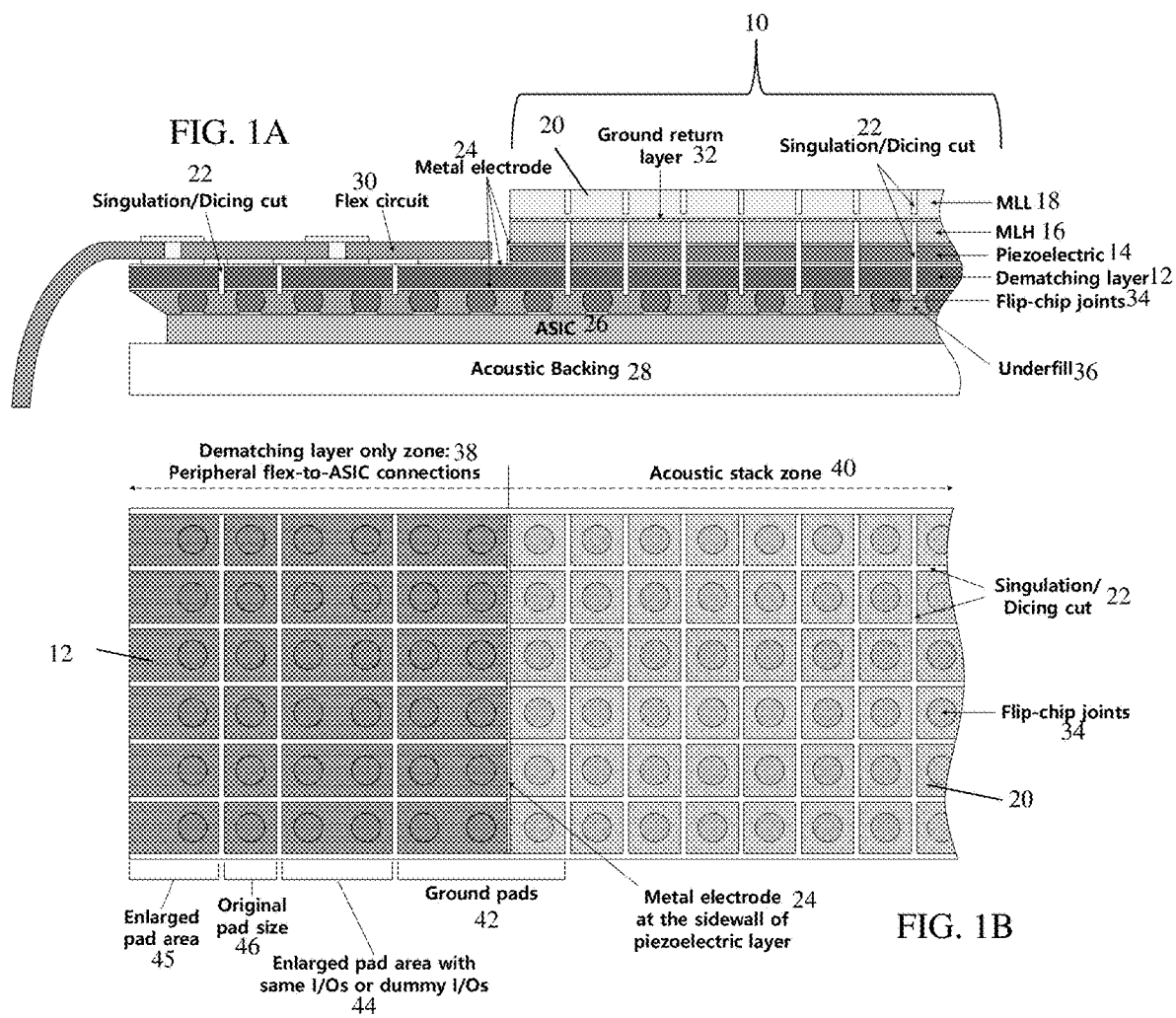

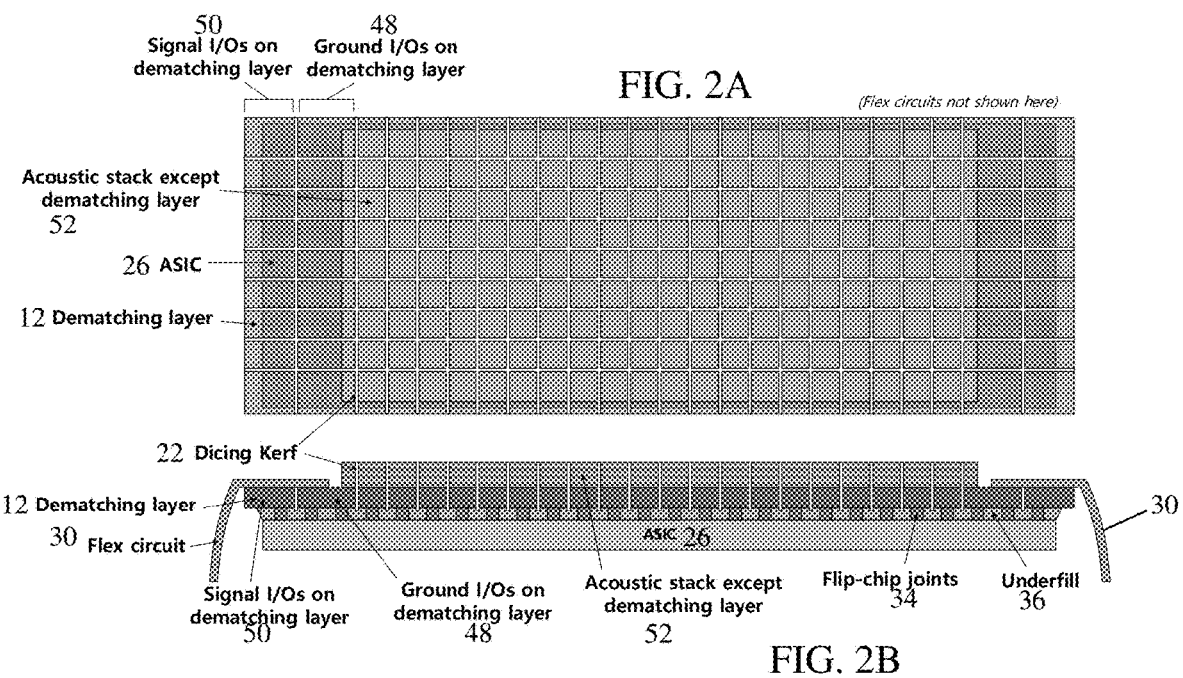

DIRECT CHIP-ON-ARRAY FOR A MULTIDIMENSIONAL TRANSDUCER ARRAY

BACKGROUND

The present embodiments relate to interconnection of multidimensional transducer arrays with electronics. Achieving the interconnection between an acoustic array and the associated transmit and/or receive electronics is a technological challenge for multidimensional (matrix) transducers. Hundreds or thousands (e.g., up to 10,000) of different elements distributed in two dimensions (azimuth and elevation) require interconnection along the z-axis (depth or range) for at least the elements surrounded by other elements. Since the elements are small (e.g., 100-500 um), there is limited space for separate electrical connection to each element.

A typical ultrasound imaging system has a limited number of channels from 64 up to 256, determined by the number of cables, through which the system communicates with an ultrasound transducer. The limited number of cables cannot transmit voltages from the system to all the acoustic elements in a matrix transducer and then receive signals back from the elements. To reduce the number of signals, a micro-beamforming application specific integrated circuit (ASIC) is used to beamform in the transducer probe. The ASIC is placed as close to the acoustic elements as possible. In a chip-on-array (COA) approach, the acoustic array is built-up directly on an ASIC chip's input/output (I/Os), such as using flip-chip connections. The COA approach contains two critical interconnections: (1) ASIC-to-acoustic element I/Os in the middle area of ASIC and (2) flex-to-ASICs interconnections in the peripheral area of ASICs. 1:1 direct interconnections for ASIC-to-acoustic I/Os are typically made by flip-chip technologies. The flex-to-ASIC interconnections are to send/receive power/ground, beamformed output and control signals back and forth between transducer and ultrasound system.

Where the acoustic stack is built only in a portion of the ASIC while the area around the perimeter of ASIC chips is reserved for flex-to-ASIC connections, pressure applied in laminating several acoustic layers together may damage the active transistor circuitry of the ASIC, such as cracking the chip at a border line where the acoustic stack ends and peripheral flex-to-ASIC bonding zones starts. The front side of the ASIC containing critical active circuitry is directly exposed to mechanical stress, various chemicals (epoxy, underfill, solder flux, etc.) and electrostatic discharge (ESD) throughout the transducer formation process. Due to die-attach machine capability and flowability of die attach materials, chip shift or off-set cannot be avoided during chip tiling (or die attach) process, which can result in inconsistent electrical pitches across the tiled chips for flex-to-ASIC connections.

The flex-to-ASIC connections are made after completing the acoustic build process, so the epoxy used to form the array and the Curie temperature of the piezoelectric limit the connection process to 100° C. or lower, yet the ASIC has an uneven surface that is best electrically connected using higher temperature processes. The flex-to-ASIC connections require a large keep-out distance to avoid contamination by underfill used in the flip-chip connection for the ASIC-to-acoustic element I/Os. Flex-to-ASIC joints might require larger pads to get reliable electrical connections due to dimensional instability of flex circuits compared to ASIC-to-acoustic I/O connections where both acoustic stack and ASICs are rigid and dimensionally stable. When the solder joints are considered for both ASIC-to-acoustic stack and flex-to-ASIC connections, it is not easy to grow different sizes of solder bumps on one wafer as different pad size changes bumping plating process conditions.

SUMMARY

By way of introduction, the preferred embodiments described below include methods, systems, transducer probes, and components for direct COA for a multi-dimensional transducer array. The generally rigid and conductive dematching layer is extended beyond a footprint of the transducer array. The ASIC is directly connected to the dematching layer on one side, while the other side provides for electrical connection to the elements of the array and I/O pads for connections (e.g., flex-to-dematching layer) to the ultrasound imaging system. By using the dematching layer rigidity, the ASIC may be protected during formation of the acoustic stack. By using the dematching layer conductivity, any misalignment is compensated by the routing through the dematching layer. By using the dematching layer conductivity, a large flat region is provided for I/O, allowing for good low temperature asperity contact connections with larger area than flip-chip solder bumps. By providing the I/O for the system connections on a different side of the dematching layer than the ASIC, a large keep-out distance due to underfill may be avoided.

In a first aspect, a multidimensional transducer array system is provided. An acoustic array has transducer elements distributed in a grid over first and second dimensions. The acoustic array has a first extent of the transducer elements along the first dimension. A dematching layer connects with the acoustic array in an acoustic stack. The dematching layer supports the transducer elements on a first side and extends by a second extend along the first dimension. The second extent is greater than the first extent. A chip of an application specific integrated circuit directly bonds to a second side of the dematching layer. The second side is opposite the first side. A flexible circuit connects to the dematching layer on the first side.

In a second aspect, an ultrasound transducer probe is provided. A chip-on-array arrangement of a semiconductor chip electrically connected to a multi-dimensional transducer array is provided. The multi-dimensional transducer array is a quarter wavelength transducer with a dematching layer. The semiconductor chip electrically connects to the multi-dimensional transducer array through the dematching layer. Contact pads are on the dematching layer for ground and signaling from the semiconductor chip to an ultrasound imaging system. The dematching layer provides signal routing from the contact pads to the semiconductor chip and from the semiconductor chip to the multi-dimensional transduce array.

In a third aspect, a method is provided for connecting electronics with an array of acoustic elements. An integrated circuit connects directly to a first surface of a dematching layer of the acoustic elements. Conductors connect to a second surface of the dematching layer. The second surface is opposite the first surface. The conductors connect to pads on the second surface outside of a footprint on the dematching layer of the acoustic elements.

The present invention is defined by the following claims, and nothing in this section should be taken as a limitation on these claims. Further aspects and advantages of the invention are discussed below in conjunction with the preferred embodiments and may be later claimed independently or in combination. Different embodiments may achieve or fail to achieve different objects or advantages.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIGS. 1A and 1B are a cross-section view and a top region view, respectively, of part of one embodiment of a chip-on-array interconnection of an acoustic array with an integrated circuit;

FIGS. 2A and 2B are a top region view and a cross-section view, respectively, of the embodiment of the chip-on-array interconnection of FIGS. 1B and 1A;

DETAILED DESCRIPTION OF THE DRAWINGS AND PRESENTLY PREFERRED EMBODIMENTS

Figures 3A, 3B:
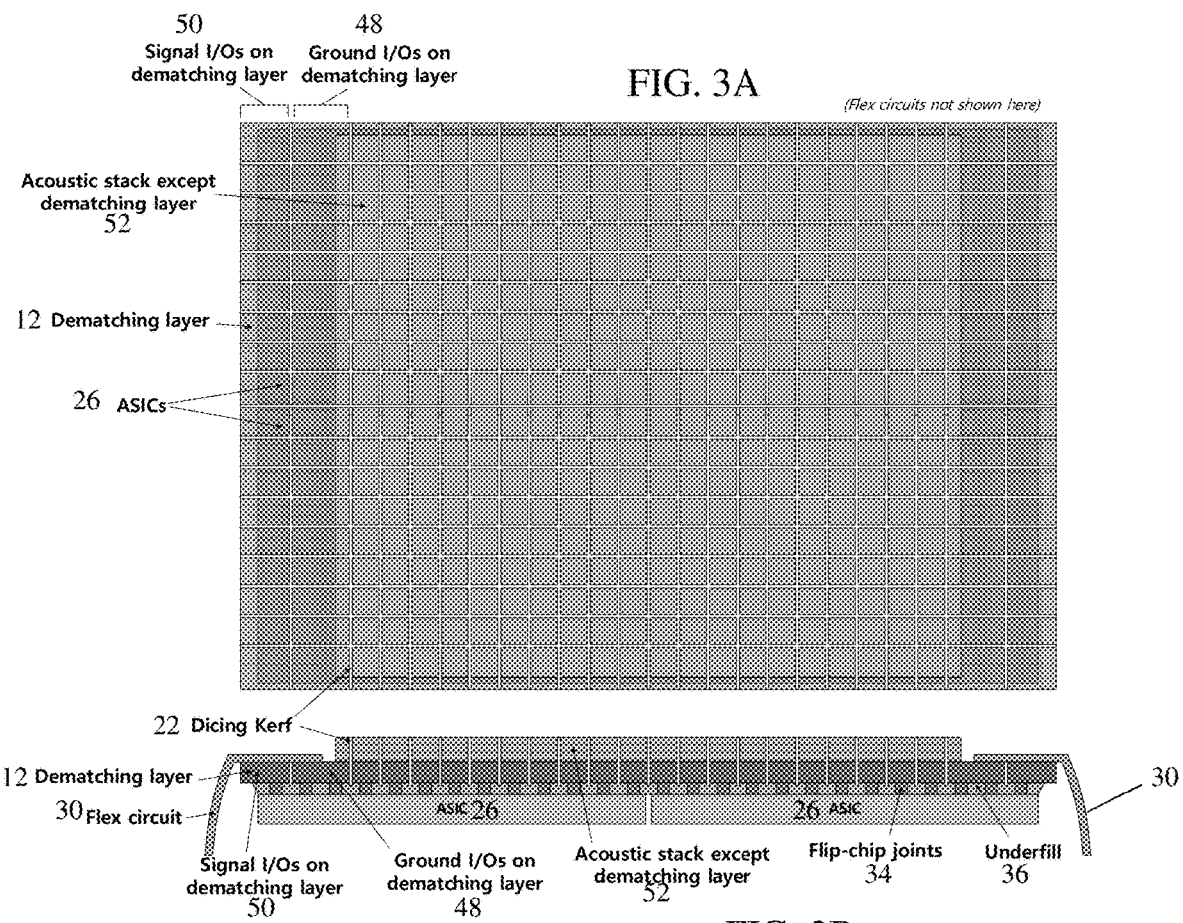
FIGS. 3A and 3B are a top region view and a cross-section view, respectively, an ultrasound transducer system using a dematching layer for connection with multiple ASICs.

The dematching layer of the acoustic stack enables a quarter wavelength acoustic design. The dematching layer is extended to cover more than the transducer elements, such as extended to cover the whole area of the ASIC or ASICs. The dematching layer is a rigid substrate that acts as a mechanical supporter for attaching to the ASIC and the rest of the acoustic stack, allowing for use of thinner ASICs. The dematching layer also acts as an electrical routing layer to send and/or receive signals and grounds, such as providing for direct connections from the ASIC to the singulated elements as well as routing signals and ground from the flexible circuit to the ASIC in the region of the dematching layer extending beyond the rest of the acoustic stack. Since the ASIC is bonded to a bottom of the dematching layer and the flexible circuit connects to a top of the dematching layer, the flex-to-ASIC bonding is more independent of the flip-chip process and to larger pads formed by the dematching layer. By connecting the flexible circuit to the extended dematching layer, low temperature asperity bonding may be used for the flex-to-ASIC electrical connections. Due to the hardness of the dematching layer, the ASIC and/or acoustic stack may be tested with less risk of the probes harming the contact pads.

FIGS. 1A and 1B show one embodiment of the schematic concept of COA interconnections. The dematching layer 12, which is the bottommost layer of an acoustic stack (e.g., the dematching layer 12, piezoelectric 14, one or more matching layers 16, 18, and electrodes 24), extends to cover the whole area of ASIC 26. All ASIC I/Os for both acoustic elements and peripheral connections are directly connected to the bottom of the dematching layer 12 so that all active circuitry of the ASIC 26 is well secured by being supported and/or protected with the substrate of the dematching layer 12. During singulation or dicing of the acoustic stack, all the ASIC I/Os (e.g., flip chip joints 34) become electrically separated by the kerfs in the dematching layer. The separated I/Os in the peripheral area of the dematching layer 12 (i.e., the area 38 extending beyond a footprint or zone 40 of the acoustic stack) connect with the flexible circuit 30. The flexible circuit 30 is electrically connected to send and/or receive various signals back and forth between the transducer and ultrasound system. Example signals routed through the dematching layer include power, ground, beamformed output signals, digital input and/or output, digital clock, and/or temperature sensor signals.

The dematching layer 12 not only enables a quarter wavelength acoustic design, but also acts as a mechanical supporter for the ASIC 26 and acoustic stack. The dematching layer 12 even acts as an electrical routing layer to send and/or receive signals and grounds toward to flexible circuit 30. The join process for the connection from the flexible circuit 30 to the I/O pads or elements of the dematching layer 12 are less affected by flip-chip joints on the opposite side of the dematching layer 12. Epoxy asperity bonding, which is a low temperature bonding process (~60° C.), may be utilized since the dematching layer 12 provides a very flat surface as opposed to flip-chip or wirebonding pads having topography around pads being protected by passivation layer on ASICs. Typical flip-chip options, such as solder, Cu- and Au-pillar, ACF, NCF, NCP and Ag paste, may be used depending on the transducers.

FIG. 1A is a cross-section view of one embodiment of a multidimensional transducer array system. The system is used for an ultrasound transducer probe, such as in a handheld probe for scanning from an exterior of a patient or an intra-cavity (e.g., transthoracic or transesophageal transducer probe) or catheter-based probe for scanning from within a patient. The system is a chip-on-array arrangement where a semiconductor chip (e.g., ASIC 26) electrically directly connects to the dematching layer 12 of a multidimensional transducer array 10. Due to the low parasitic, short electrical connections, improved scanning and imaging with ultrasound may be provided for medical diagnosis. The dematching layer 12 is extended to provide for electrical connection to the flexible circuit 30 as well as to protect the semiconductor chip.

Figure 8:
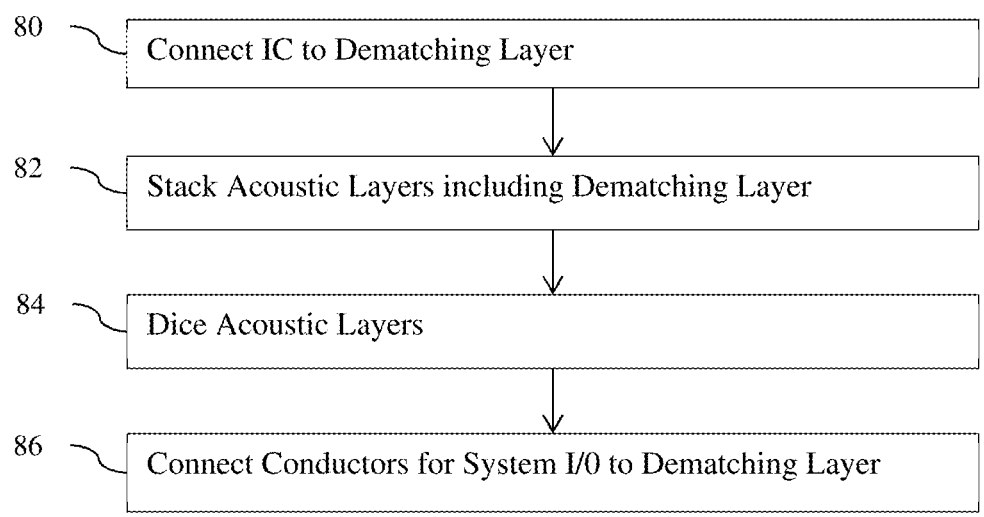
FIG. 8 is a flow chart diagram of one embodiment of a method for connecting electronics with an array of acoustic elements.

The array system and corresponding probe are formed using the method of FIG. 8 or another method. The array system includes the array 10 formed by an acoustic stack, the ASIC 26, and the flexible circuit 30. Additional, different, or fewer components may be provided. For example, the acoustic backing 28 to absorb acoustic energy is added to the back of the ASIC 26. As another example, the flexible circuit 30 is not provided, such as where wirebond or other electrical connection is provided between the ASIC 26 and the ultrasound imaging system or scanner.

The acoustic array 10 has transducer elements 20 distributed in a grid over two dimensions. The multidimensional transducer array 10 is an array of piezoelectric or micro-electromechanical (capacitive membrane) elements 20. Piezoelectric examples are used herein. The array 10 is flat, concave or convex. The elements 20 are distributed along azimuth and elevation dimensions. The elements 20 are distributed with any of various pitches, such as every 100, 150, 200, 250, 400 or 500 micrometers, in a fully sampled spacing along the two dimensions. In FIGS. 1A and 1B, the pitch of the transducer elements 20 is shown as a same pitch (e.g., center-to-center) pitch as the flip-chip joints 34. Other pitches or a pitch that varies as a function of location may be used. The pitch may be the same or different in different directions or dimensions, such as 300 micrometers along elevation and 600 micrometers in azimuth. Full or sparse sampling of placement of the elements 20 is provided.

The array 10 and corresponding transducer elements 20 include one or more impedance matching layers 16, 18, a piezoelectric layer 14, and the dematching layer 12. Each of the elements 20 of the array 10 includes at least two electrodes. The elements 20 transduce between electrical and acoustical energies. Additional, different, or fewer layers may be provided. For example, a backing block 28 may be positioned on one side of the array 10 for limiting acoustic reflection from energy transmitted in an undesired direction. A lens, a window, or other now know or later developed multidimensional transducer array components may be included.

The matching layer 16, 18 is a ¼ wavelength thickness layer of material. The material has an acoustic impedance between the impedance of the piezoelectric layer 14 and the patient. Multiple layers for a gradual change in acoustic impedance may be used, such as shown with the high and low matching layers 16, 18. Only one matching layer 16, 18 may be used.

The piezoelectric layer 14 is a slab or plate of piezoelectric material. A solid piezoelectric (e.g., single crystal PZT) may be used. Single or poly-crystal piezoelectric material may be used. In other embodiments, a composite of piezoelectric and epoxy or another polymer is used.

A grounding plane may form one electrode. The grounding plane may be provided by a conductive matching layer 16, 18. Either or both of the matching layers 16, 18 may be conductive, such as providing a grounding plane as well as impedance matching. Alternatively or additionally, a separate metalized layer or foil layer is provided as the ground plane for the array 10. A sheet of conductor is placed or deposited on, within, or below one of the matching layers 16, 18, such as the ground return layer 32 between the matching layers 16, 18 as shown in FIG. 1A.

Another sheet of conductor provides conductors to form the signal electrodes. Conductor deposited on the dematching layer 12 or the piezoelectric layer 14 may be used. Alternatively, conductor placed or formed between the dematching layer 12 and the piezoelectric layer 14 is used. In yet other embodiments, the conductor is formed by conductive material of the dematching layer 12. Once diced or separated, the sheet of conductor provides separate signal electrodes for the transducer elements 20. An electrically separate signal electrode is provided for each transducer element 20.

The acoustic stack forms a quarter wavelength transducer. The elements 20 of the array 10 include the dematching layer 12, which allows a thickness of the piezoelectric layer 14 based on quarter wavelength design. An acoustic backing 28 may be added behind the ASIC 26.

The transducer elements 20 include the dematching layer 12. The kerfs 22 (dicing cuts) that separate the elements 20 extending through the dematching layer 12. In the acoustic stack, the transducer elements 20 of the array 10 have the piezoelectric layer 14 connect to or stacked on one side of the dematching layer 12. The dematching layer 12 supports the transducer elements 20. A top or transducer facing surface of the dematching layer 12 contacts the signal electrode and/or piezoelectric layer 14, while a bottom or rear facing surface of the dematching layer 12 contacts the ASIC 26.

The de-matching layer 12 is a ¼ wavelength thickness layer of material. Any material may be used, such as tungsten carbide, where the material provides for a greater acoustic impedance than the piezoelectric 14 of the elements 20. The de-matching layer 12 provides a clamped boundary condition, leading to better sensitivity and wider bandwidth in the ultrasound transducer.

Referring to FIGS. 1B, 2A and 2B, the elements 20 of the acoustic stack 52 cover an array zone 40. The elements 20 are distributed along the azimuth and elevation dimensions over the array zone 40, forming a footprint of the array 10. The dematching layer 12 has a greater extent along at least one of the dimensions. For example, FIG. 1B shows the dematching layer 12 covering both the acoustic stack zone 40 and a dematching layer only zone 38. Rather than having a same footprint as the acoustic stack, the dematching layer 12 has a greater area and extends to have a greater length along the elevation or azimuth dimension. As another example, FIGS. 2A and 2B show the dematching layer 12 having a slightly greater extent than the acoustic stack 52 along one dimension (e.g., elevation) and a substantially (at least 10%) greater extent than the acoustic stack 52 along another dimension (e.g., elevation). The array 10 has a lesser extent in azimuth and/or elevation than the dematching layer 12.

In one embodiment, the dematching layer 12 has a same area or size and shape as the ASIC 26. The ASIC 26 has a greater footprint than the acoustic stack 52, so extends along one or two dimensions to a greater extent than the array 10. The dematching layer 12 may have a lesser or greater area than the ASIC on the mated or contacting surfaces. FIGS. 2A and 2B show the ASIC 26 as having a greater area (e.g., length and width) than the acoustic stack 52 and show the dematching layer 12 as having a grater area (length and width) than the ASIC 26.

The dematching layer 12 is rigid, such as having a stiffness or elastic modulus greater than 400 GPa (e.g., >530 GPa in elastic modulus). The dematching layer 12 is electrically conductive and/or is plated or has vias formed therein for electrical conduction. The dematching layer 12 acts as a rigid and dimensionally stable substrate throughout not only flip-chip process of connecting the ASIC 26 to the acoustic elements 20 (i.e., connecting the ASIC 26 to the acoustic stack 52) but also during the array lamination process. The ASIC 26 attaches to the lower surface of the dematching layer 12 by one of various flip-chip options, including solder, Cu- and Au-pillar, epoxy asperity bonding, ACF, NCF, NCP and Ag paste. During the flip-chip process, the whole ASIC 26 is well supported by this rigid substrate (i.e., dematching layer 12). While acoustic layers (e.g., piezoelectric 14, ground return, shield layer, and matching layers 16, 18) are laminated together on the upper surface of dematching layer 12, the lamination pressure is well distributed through this extended rigid dematching layer 12 over the ASIC 26 without stress concentration points. The rigid substrate provided by the dematching layer 12 supports the whole chip area of the ASIC 26, allowing for a thinner ASIC 26 to avoid any unwanted ultrasound wave reflection from the chip.

The ASIC 26 is a semiconductor chip. The semiconductor chip includes an integrated circuit for signal processing. Transistor based, or switch-based devices, are provided within the chip. The integrated circuit may be the ASIC 26. In other embodiments, the chip or integrated circuit includes an analog circuit, digital circuit, switch, multiplexer, controller, processor, digital signal processor, field programmable gate array, or other now known or later developed active electrical component. The integrated or other circuit may be in a semiconductor chip form as the circuit.

The semiconductors or active electronics include transmit and/or receive circuits for ultrasound scanning with the acoustic array 10. For example, a plurality of transmit circuits, a plurality of receive circuits, and/or a controller is provided as a semiconductor chip. The transmit components are separate from or may be integrated with the receive components. Transmit components include high voltage pulsers, filters, memories, delays, phase rotators, multipliers, combinations thereof, or other now known or later developed transmit beamformer component. The receive components include filters, amplifiers, delays, summers, combinations thereof, or other now known or later developed receive beamformer component. Since receive beamformer components may operate at lower voltages than the transmit components, the receive and transmit components are on separate devices or chips, but a combination device for the transmit and receive operation may be provided. The integrated circuit includes all or part of a transmit beamformer, pulsers, receive beamformer, amplifiers, phase rotators, delays, summers, or other active electronics used for ultrasound scanning. For example, the ASIC 26 is a partial beamformer for combining signals from different groups of elements and outputting a number of partially beamformed signals for different receive apertures to the corresponding number of traces on the flexible circuit 30 and cables connecting the probe to the ultrasound system and the beamformer therein.

In one embodiment, a single active electrical component, such as a single chip or ASIC 26, is provided as shown in FIGS. 2A and 2B. A larger number of acoustic elements 20 and corresponding aperture result in a larger sized ASIC chip to handle the acoustic signals. A larger ASIC chip is more expensive since the larger chip has more chances to have defects during semiconductor processing. To reduce the size of the integrated circuit, two or more integrated circuits may be tiled. FIGS. 3A and 3B show an example where four semiconductor chips or integrated circuits are tiled. Two or more semiconductor chips may be tiled or placed adjacent each other. Each semiconductor or integrated circuit is positioned adjacent to the dematching layer 12. Two or more smaller sized chips are mounted on to the dematching layer 12 instead of a single larger ASIC chip. Each integrated circuit electrically connects with different sub-sets of the transducer elements 20. For example, four ASICs 26 electrically connect to four groups of elements 20 where each element 20 is in only one group. Whether tiled or not, the dematching layer 12 acts as a mechanical supporter for attachment of the ASICs 26 and the acoustic stack as well as an electrical routing layer to send/receive signals and grounds toward to flex circuit 30.

Figure 4:
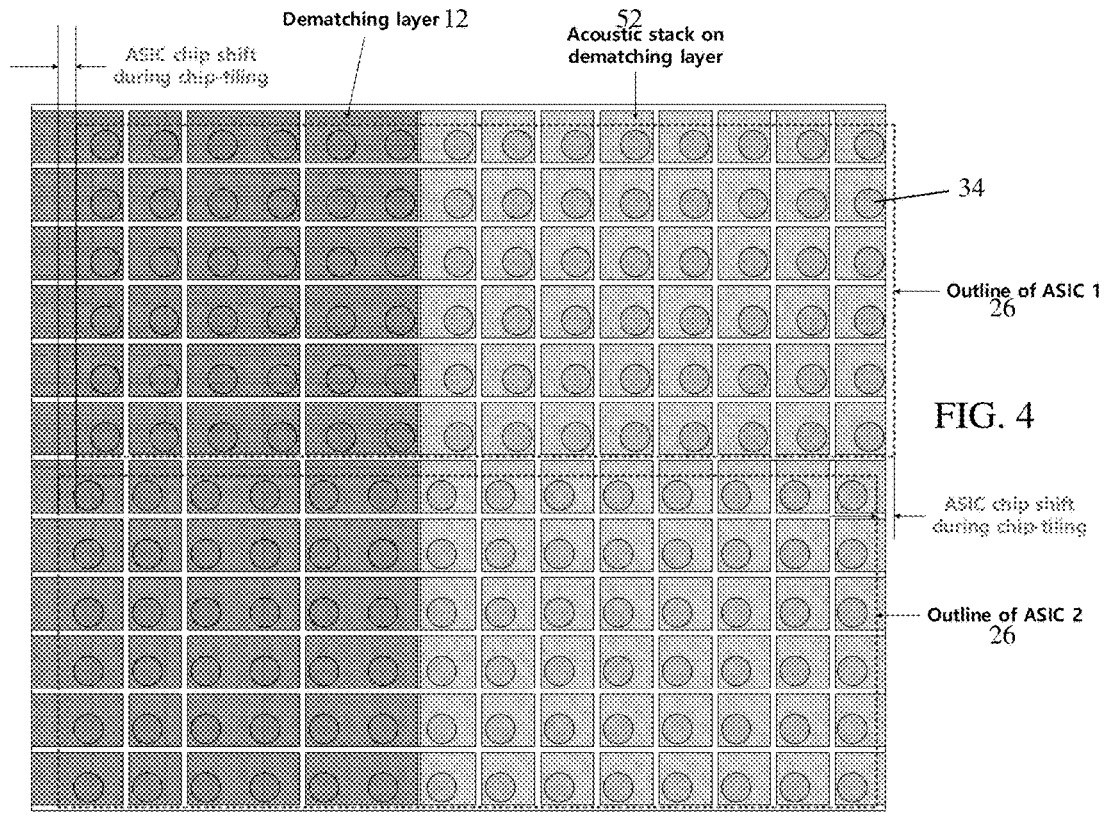
FIG. 4 shows an example of chip shift allowed due to using an intervening dematching layer.

As more ASICs 26 are mounted underneath the acoustic stack with increased acoustic aperture, the continuity of pitch is more likely to be broken due to chip shift across the tiled chips. FIG. 4 shows an example where the outlines of two ASICs 26 are shown with dashed lines. These ASICs 26, as tiled, are shifted relative to each other and the dematching layer 12. Since the dematching layer 12, as kerfed, forms larger surface area pads or signal paths, some shift may be provided while still connecting the flip chip joints 34 to the correct elements 20 and pads formed by the dematching layer 12 for connection with the flexible circuit 30. The dematching layer 12 provides for consistent pitches corresponding to the flex circuit pads and acoustic elements 20 despite the shifts of the ASICs 26. The pitches for flex-to-ASIC input/outputs and for the element-to-ASIC input/outputs can be reset and continuous through the dematching layer 12 as input/output elements in spite of die attach shift during ASICs tiling.

Referring to FIGS. 1A and 1B, the semiconductor chip (e.g., ASIC 26) includes input/output pads. The semiconductor chip includes input/output conductors exposed on a largest surface or surface to be placed against the dematching layer 12. In alternative embodiments, the pads exit the chip alongside edges and are routed by wire bond or redistributions layers comprising sequentially deposited metal traces and dielectric to a distribution on the largest surface. For connection to the dematching layer 12, flip-chip joints 34 are formed on the input/output pads. The flip-chip joints 34 are solder balls, Cu-pillar, Au bump, Ag paste or an anisotropic conductive film (ACF).

The semiconductor chip (e.g., ASIC 26) is directly flip-chip bonded to the dematching layer 12. The chip is placed against the dematching layer 12 so that the flip-chip joints 34 contact the dematching layer 12 with no intervening layers. This direct connection may include underfill 36 to support the flip-chip bonding. Heat is applied, forming a direct physical and electrical connection from the chip (e.g., from the input/output pads of the ASIC 26) to the dematching layer 12. The semiconductor chip is directly bonded to a bottom or side opposite the piezoelectric layer 14 of the dematching layer 12. This bonding may be performed before stacking the rest of the acoustic stacking layers.

As shown in FIGS. 2A and 2B, the semiconductor chip (e.g., ASIC 26) has a larger surface area than the footprint of the array 10. The acoustic stack 52 forming the elements 20 of the array 10 has a given size of the surface connecting to the dematching layer 12. The semiconductor chip has a larger size of the surface connecting to the dematching layer 12. The chip is larger along at least one dimension, such as along azimuth or elevation. The chip may be larger along both azimuth and elevation. The chip is a same size (e.g., same surface area) and shape as the dematching layer 12. Alternatively, and as shown in FIGS. 2A and 2B, the contact surface of the chip is smaller than the contact surface of the dematching layer 12.

In one embodiment, the dematching layer 12, acoustic array 10 (e.g., acoustic stack 52 without the dematching layer 12), and chip (e.g., ASIC 26) have extents along the elevation dimension within 5% of each other (i.e., the shortest is within 5% of the longest along elevation). Other relative sizes, such as equal, within 2%, or within 10% may be used. The dematching layer 12 and chip are at least 10% greater than the length of the acoustic stack 52 along the azimuth dimension. Other relative sizes, such as 5%, 15%, or 20%, may be used. The dematching layer 12 may extend in elevation instead or in addition to azimuth. The dematching layer 12 and the chip have extents along the azimuth and/or elevation dimensions within 5% of each other and at least 10% greater than the extent of the acoustic stack 52 along one or both dimensions. Other relative sizes may be used.

Referring to FIGS. 1A and 1B, the flip-chip joints 34 are positioned to connect the input/output pads of the ASIC 26 to the elements 20. Separate flip-chip joints 34 connect with separate elements 20 in the acoustic stack zone 40. In the dematching layer only zone 38 (i.e., no piezoelectric layer 14 or outside of the footprint of the array 10), other flip-chip joints 34 are positioned to connect for communications or signals with the ultrasound scanner. For example, separate flip-chip joints 34 electrically connect power, ground, beamformed output, and clock signals to the flexible circuit 30 through the dematching layer 12. Some of the flip-chip joints 34 may be connected for the same signal, such as two or more flip-chip joints 34 being on a same input/output pad of the ASIC 26 or different input/output pads of the ASIC for a common signal. As shown in FIG. 1B, some flip-chip joints 34 may connect to ground for the edge elements 20 of the acoustic stack, and some flip-chip joints 34 may connect to ground for the flexible circuit 30.

Since the dematching layer 12 is conductive, the dematching layer 12 acts as an electrical routing layer to send and receive signals and ground from the elements 20 and the flexible circuit 30. The dematching layer 12 may be plated to assist in electrical connection. The dematching layer 12 provides signal routing from the contact pads of the flexible circuit 30 to the semiconductor chip (e.g., ASIC 26) and from the semiconductor chip to the multi-dimensional transduce array 10. The dematching layer 12 provides for pad redistribution, acting as a redistribution layer. The semiconductor chip (e.g., ASIC 26) electrically connects to the multi-dimensional transducer array 10 (i.e., electrically connects to the elements 20) and to the flexible circuit 30 through the dematching layer 12.

Kerfs 22 (e.g., singulation or dicing cuts) are formed in the dematching layer 12. The layers of the acoustic stack are added to the dematching layer 12. Once added, the stack, including the dematching layer 12, are diced. One or more matching layers 16, 18 and/or a ground return layer 32 may not be diced. For the acoustic stack, the dicing and resulting kerfs 22 separate the acoustic elements 20 of the array 10. The kerfs 22 extend through the dematching layer 12 so that separate electrical connections from the ASIC 26 and flip-chip joints 34 are provided for the elements 20. The signal passes through the separated conductive dematching layer 12. The transducers elements 20 formed by the dicing kerfs 22 have a first pitch along one or both dimensions. The pitch is equal along azimuth and elevation, but different pitches may be provided.

The dicing also forms kerfs 22 in the dematching layer zone 38 where there is no piezoelectric layer 14 (i.e., outside the footprint of the array 10). These kerfs 22 through the dematching layer 12 in the region extending beyond the transducer elements 12 form contact pads for the flexible circuit 30. The pitch along one or more dimensions for the kerfs 22 and resulting contact pads is the same or different than the pitch for the elements 20. For example, the pitch is double along the azimuth dimension for at least some of the pads formed from the dematching layer 12.

In one embodiment, the separation of the dematching layer 12 by the kerfs 22 forms one or more ground pads 42, power pads, control signal pads, partial beamformer output pads, and/or transmit signal pads. The kerfs 22 form contact pads for the flexible circuit 30. While the acoustic elements 20 are created by singulating/dicing laminated acoustic layers according to the ASIC pitch, the peripheral area of dematching only layer zone 38 is also diced, which will in turn create contact pads or input/output elements. The ASIC peripheral input/outputs are connected to pads on the flexible circuit 30 through these dematching layer-based input/outputs. The singulation/dicing is deep enough to cut through the dematching layer 12 but not reach ASIC top surface.

The contact pads formed by dicing the dematching layer 12 are larger than the flip-chip joints 34. The separated parts of the dematching layer 12 are themselves the contact pads for the flexible circuit 30 and the elements 20. Metallization on the dematching layer 12 may be used to form better conductive bonds. The contact pads (e.g., 42, 44, 45, 46) for connecting with the flexible circuit 30 are on a same surface of the dematching layer 12 as the acoustic stack, opposite the surface of the dematching layer 12 for the flip-chip bonding.

The kerfs 22 separate the dematching layer 12 to provide pads for ground and signaling between the semiconductor chip and the ultrasound imaging system. Different arrangements may be used to form a pad. FIG. 1B shows some examples, such as the ground pads 42 formed to connect with flip-chip joints 34 connected to ground of the ASIC 26. In another example, one or more of the flip-chip joints 34 is a dummy input/output. The pad size (e.g., pads 44) can be increased by merging the same ASIC input/outputs together or incorporating some dummy input/outputs on the ASIC 26. The resulting pad of the dematching layer 12 connects to one or more dummy input/outputs of the ASIC 26 and one or more signal input/outputs. The pads formed by the kerfs 22 in the dematching layer 12 may have any of various sizes, such as the original pad size 46 corresponding to a pitch of the flip-chip joints 34 or elements 20 or as the double pad size of the enlarged pad area 45. In the example of FIG. 1B, the outermost pads 45 extended further beyond ASIC input/outputs by using slightly larger size of dematching layer than the pitch of the input/output pads of the ASIC 26. A larger size pad may connect to one, two, or more flip-chip joints 34. While the size and pitch of the contact pads formed from the dematching layer 12 may correspond to the input/output pads of the ASIC 26, the size and/or pitch may be different and/or vary. A semi-redistribution layer can be defined in the dematching layer 12, depending on the location of dicing cuts and resulting kerfs 22. The redistribution provides flexibility of pitch and pad size in the ASIC joint process with flexible circuits 30.

The flexible circuit 30 connects to the dematching layer 12 on the same side as the piezoelectric layer 14 and opposite side from the ASIC 26. The flexible circuit 30 is an electrically insulating or dielectric material. In one embodiment, the flexible circuit 30 is a flexible sheet of polyimide. Traces or other conductors may be included on and/or in the flexible circuit 30, such as deposited and/or etched copper traces. Passive and/or active electronics may or may not be attached. The traces route signals between the ASIC 26 and the ultrasound scanner or imaging system. For example, the flexible circuit 30 connects with cables of the transducer probe, which cables connect with the ultrasound scanner.

Figure 5:
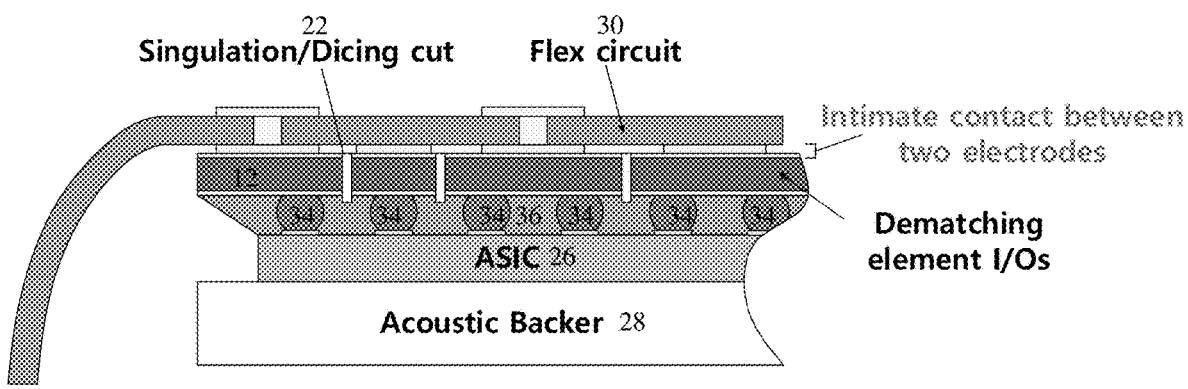
FIG. 5 illustrates an example of asperity contact provided on a surface of a dematching layer.

Referring to FIG. 5, the flexible circuit 30 has traces or contact pads that connect with the contact pads formed on or by the dematching layer 12. FIG. 5 shows use of vias through the flexible circuit 30 for signal routing from some of the contact pads of the dematching layer 12.

The flexible circuit 30 is bonded to the dematching layer 12. Any material for bonding may be used. In one embodiment, the material is a low-temperature curable polymer, such as epoxy, polyurethane, polyester, Ag paste, or other polymer-based material. Low temperature is relative to the transducer elements 20. The Curie temperature of the piezoelectric layer 14 may be between 80-120° C. For example, a binary single piezo-crystal has a Curie temperature of 80° C., and a ternary single piezo-crystal has a Curie temperature of 120° C. Other Curie temperatures may be provided. Other temperatures related to change in operation or breakdown of any of the layers in the acoustic stack may be used. Reaching or exceeding the temperature is undesired in forming the COA transducer system. The material for bonding or other interconnection allows for connection without exceeding the low temperature.

In one embodiment, asperity contact and bonding are provided. The flexible circuit 30 is stacked with or laid against the dematching layer 12 after the kerfs 22 are formed. The material for bonding is added to or during the stacking. The material may cure at room temperature or an elevated temperature below the Curie temperature or other breakdown temperature. For example, two metal pads are in intimate contact to each other, and then are bonded together by cured epoxy by or on the two pads. A low temperature bonding process around ~60° C. is used. The flexible circuit 30 connects by asperity contact to the contact pads, forming an intimate contact between electrodes for electrical conductivity. Alternatively, flip-chip options, such as solder, Cu- and Au-pillar, ACF, NCF, NCP and Ag paste, may be used to connect the flexible circuit 30 to the matching layer 12.

High temperature (e.g., >120° C.) interconnection may be used for the flip-chip connection by performing this connection prior to connecting the acoustic stack or flexible circuit 30. High temperature reliable electrical interconnections (>120° C.) include lead and lead-free solder (>180° C.), Cu pillar with solder cap (>250° C.), and high temperature anisotropic conductive film (ACF) (>120° C.).

Since the flexible circuit 30 connections are to the dematching layer 12 on the backside of where the flip-chip joints 34 are made, this flexible circuit join process is not quite affected by the front ASIC flip-chip process. The backside pads have less chance to get contaminated by underfill 36 flow dispensed in the front during the flip-chip process and their pad metallurgy or finish process do not need to be compatible with the front side. In addition, no keep-out zone to prevent contamination of peripheral pads from flow of the underfill 36 is required. Further, being independent of ASIC flip-chip joints 36, various joint options that are specifically appropriate for the flexible circuit-to-dematching layer connections may be used, such as the epoxy asperity bonding. Since the dematching layer 12 provides a flat surface as compared to contact pads on the ASIC 26 where the passivation layer may interfere, the asperity contact is more likely to be sufficient.

As shown in FIGS. 1A, 2B, 3B, 6, and 7, the flexible circuit 30 may connect to the dematching layer 12 adjacent to the acoustic stack. Since the underfill 36 is on an opposite side of the dematching layer 12, a zone to allow flow of the underfill 36 is not needed. The flexible circuit 30 and one or more contact pads of the flexible circuit 30 may connect to the dematching layer 12 within one element width of the acoustic stack. Greater or lesser separation from the flexible circuit 30 and the piezoelectric layer 14 may be provided, such as abutting or contacting each other.

Figure 6:
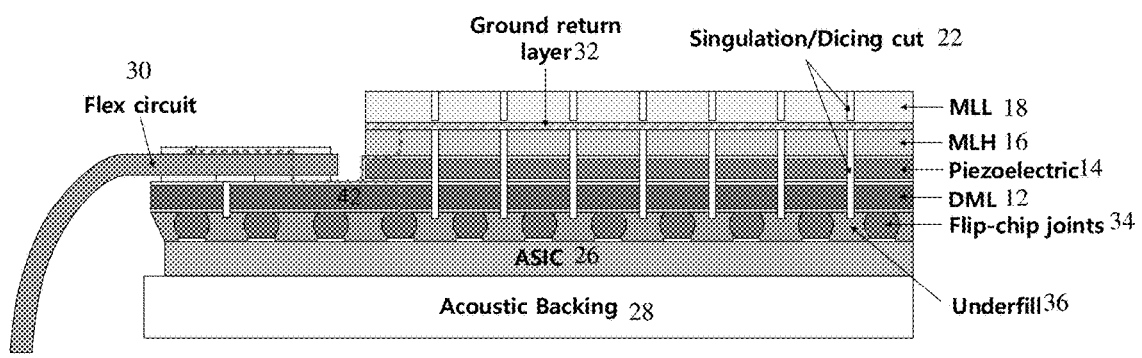
FIG. 6 illustrates example grounding paths provided due to use of the dematching layer for signal routing.

Due to the conductivity of the dematching layer 12, one or more grounding paths from the flexible circuit 30 to the ground return layer 32 of the acoustic stack may be formed. One ground path may not pass through the semiconductor chip (ASIC 26). FIG. 1B shows forming ground pads 42 from the dematching layer 12. The ground trace of the flexible circuit 30 connects to the ground pad 42. A ground connection of the array 10 also connects to the ground pad 42, such as through a metal electrode 24 formed on a side of the edge elements 20. FIG. 6 shows two ground paths with a dashed line. One ground path is from the ground return layer 32 through the conductive matching layer 18, along the electrode 24 on the side of the edge elements 20, through the dematching layer 12, and to the flexible circuit 30. Another path is through one or more flip-chip joints 34, through the ASIC 26, back through one or more other flip-chip joints 34, through the dematching layer 12, and to the flexible circuit 30.

In the acoustic stack, piezoelectric elements, a sandwich structure of two metal electrodes and piezoelectric in-between the electrodes, are operated by supplying power on the bottom electrode and returning a ground path on the top electrode. The power is supplied by the ASIC 26 through the dematching layer 12. Many ground paths are directly linked to the ultrasound system through the flexible circuit 30 and then coaxial cables.

Figure 7:
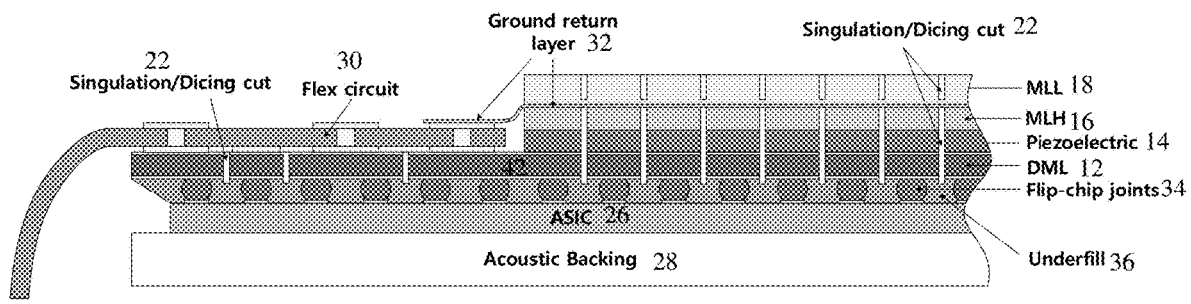
FIG. 7 illustrates another example grounding path.

FIG. 7 shows an alternative or additional ground path. Since the flexible circuit 30 may be positioned close to the acoustic stack, a bridge may be formed from or by the ground return layer 32 to the flexible circuit 30. This ground path does not pass through the dematching layer 12 or the ASIC 26. The ground return layer is directly connected to the flexible circuit 30. Ground input/outputs of the ASIC 26 may be routed through the dematching layer 12 to the flexible circuit 30.

FIG. 8 shows one embodiment of a method for connecting electronics with an array of acoustic elements. The dematching layer, as extended beyond the piezoelectric layer and/or remaining portions of the acoustic stack, is used for direct connection to the integrated circuit as well as to form contact pads for connecting with the flexible circuit or other conductors for electrical communication with the scanner.

The method is implemented as a manufacturing of the array system and/or probe. A technician or robot stacks and aligns, such as using guide posts or a frame. An oven, iron, induction solderer, or wave bath is used to bond or interconnect. A frame, housing, or holder are used to shape and position in a probe housing. A press may be used to add pressure for bonding or laminating.

Additional, different, or fewer acts may be used. For example, act 84 for dicing is not performed where the transducer stack is previously kerfed. As another example, act 86 is not performed where a sub-assembly is created.

The acts are performed in the order shown (i.e., numerical or top-to-bottom) or other orders. For example, act 80 is performed after act 84 or act 86.

In act 80, an integrated circuit is directly connected to one surface of a dematching layer of the acoustic elements. The connection is with flip-chip bonding, but other connections may be used such as asperity contact. The connection is without an intervening layer. The integrated circuit physically connects as a chip to the dematching layer with flip-chip joints. For example, Cu pillars are provided on the integrated circuit. The Cu pillars are to be used to connect the chip to the dematching layer, such as to a deposited electrode sheet of the dematching layer.

Heat may be applied to form the physical and electrical connections. For solder, heat is generated by an iron, induction solder, oven, or wave bath. For VCF or polymer, an oven or iron may be used. The heat forms the interconnection. Higher temperatures than allowed by the acoustic module may be used, such as forming reliable electrical bonding at greater than 120° C. Temperatures greater than a Curie temperature or breakdown temperature of any component of the acoustic module may be used. The interconnection is formed at the higher temperature. Lower temperatures may be used.

In act 82, other acoustic layers are stacked on the dematching layer. The piezoelectric layer, one or more matching layers, and/or ground foils are stacked. Using posts and/or a frame, the layers of the acoustic module are aligned and positioned against each other. The layers of the transducer are stacked as not yet bonded together.

The layers of the transducer are stacked on a side of the dematching layer opposite the integrated circuit. The dematching layer may protect the integrated circuit during formation of the acoustic stack.

Polymer, paste, or other material for bonding is added to the stack, such as between and/or around layers of the stack. For example, the bottom layer of the transducer (e.g., de-matching layer) is coated with epoxy. Low temperature (e.g., below a Curie or breakdown temperature of part of the acoustic module) curable polymers may be used.

The stack is pressed together by a vise to form asperity contact for electrical connections. The compressed stack is heated, such as being positioned in an oven. The temperature of the oven is below a lowest of the Curie temperature or breakdown temperature of any component of the stack. The heat increases the rate and/or strength of bonding. The heat may activate the bonding.

In one embodiment, the ground foil and/or one or more matching layers are stacked after the dicing in act 84. The ground foil and/or one or more matching layers are stacked after dicing, and then bonded to the rest of the already bonded and diced stack.

In act 84, the transducer stack is diced. A saw or laser is used to form kerfs in the stack, separating the stack into transducer elements. The dicing forms the array of acoustic elements from the piezoelectric slab.

The dicing extends through the dematching layer. The dicing forms the separate elements of the array. The dematching layer is also diced along a portion of the dematching layer extending beyond the footprint of the acoustic elements or array. This part of the dematching layer is used for connection with the ultrasound scanner. The dicing separates the dematching layer to form contact pads for connection. The integrated circuit connects to the dematching layer in the footprint of the array for transmitting and receiving signals from the elements. The integrated circuit connects to the dematching layer outside the footprint of the array for communicating with the ultrasound scanner through the contact pads formed by the diced dematching layer.

In act 86, conductors for communication with the ultrasound scanner are connected to the dematching layer. For example, traces on a flexible circuit are connected to the dematching layer.

The connection is on the portion of the dematching layer outside the footprint of the array. The connection is on a same side of the dematching layer as the piezoelectric, a side opposite the side to which the integrated circuit connects. The portion of the dematching layer extending outside the footprint of the acoustic elements, the side opposite the integrated circuit, is used for connection with the conductors.

The connection is through asperity contact. For example, an epoxy is applied. The conductors (e.g., flexible circuits with traces) are pressed onto the dematching layer, and the epoxy is cured. Heat may be applied. The connection may be formed when also forming the acoustic stack (i.e., bonded at a same time). Alternatively, the connection is later formed using no heat or heat less than the melt temperature of the epoxy used for the acoustic stack.

For this COA-type ultrasound transducer, testing may be provided in a way that avoids replacement of some expensive parts. The testing is performed before the connection of act 86 (i.e., before integrating the acoustic stack and integrated circuit with expensive components such as flexible circuits containing FPGA (Field Programmable Gate Array), MUX (Multiplexer) and SMT (Surface Mounted Technology) components and even coaxial cables). Al pad or solders are very soft so may be easily damaged during test probing. By testing using the more hard and stiff pads formed by the dematching layer (e.g., tungsten carbide (WC) is ×24 and ×260 harder than Aluminum and solder in terms of Vickers hardness, respectively), probing marks that might affect joint formation are less likely to be created during testing.

While the invention has been described above by reference to various embodiments, many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A multidimensional transducer array system, the system comprising:
   an acoustic array having transducer elements distributed in a grid over first and second dimensions, the acoustic array having a first extent of the transducer elements along the first dimension;
   a dematching layer connected with the acoustic array in an acoustic stack, the dematching layer supporting the transducer elements on a first side and extending by a second extend along the first dimension, the second extent greater than the first extent;
   a chip of an application specific integrated circuit directly bonded to a second side of the dematching layer, the second side opposite the first side; and
   a flexible circuit connected to the dematching layer on the first side.

2. The multidimensional transducer array system of claim 1, wherein the acoustic stack comprises at least one matching layer, the transducer elements, and the dematching layer, and wherein kerfs separating the transducer element also separate the dematching layer.

3. The multidimensional transducer array system of claim 1, wherein the dematching layer comprises tungsten carbide with an acoustic impedance greater than the transducer elements.

4. The multidimensional transducer array system of claim 1, wherein the chip has a third extent along the first dimension, the third extent equal to or longer than the second extent.

5. The multidimensional transducer array system of claim 4, wherein the dematching layer, acoustic array, and chip have extends along the second dimension within 5% of each other, and wherein the second and third extents are within 5% of each other and at least 10% greater than the first extent.

6. The multidimensional transducer array system of claim 1, wherein the application specific integrated circuit comprises a beamforming circuit, and wherein the chip is directly bonded with flip-chip joints, separate flip-chip joints electrically connected with separate ones of the transducer elements.

7. The multidimensional transducer array system of claim 6, wherein further separate flip-chip joints electrically connect power, ground, beamformed output, and clock signals to the flexible circuit through the dematching layer.

8. The multidimensional transducer array system of claim 1, wherein the flexible circuit connects to the dematching layer with asperity bonding, the asperity bonding electrically connecting the flexible circuit to the dematching layer, which dematching layer electrically connects to the application specific integrated circuit.

9. The multidimensional transducer array system of claim 1, wherein first dicing kerfs separating the transducer elements extend through the dematching layer, the transducers elements formed by the dicing kerfs having a first pitch along the first dimension, and wherein second dicing kerfs through the dematching layer in a region extending beyond the transducer elements along the first dimension form contact pads for the flexible circuit, the contact pads having a second pitch greater than the first pitch.

10. The multidimensional transducer array system of claim 1, wherein the flexible circuit electrically connects to the dematching layer within one element width along the first dimension of the acoustic array.

11. The multidimensional transducer array system of claim 1, wherein a first ground path from the acoustic array to the flexible circuit connects through the dematching layer without passing through the chip.

12. The multidimensional transducer array system of claim 1, wherein at least one ground path connects the acoustic array to the flexible circuit as a bridge and without passing through the dematching layer or the chip.

13. An ultrasound transducer probe comprising:
   a chip-on-array arrangement of a semiconductor chip electrically connected to a multi-dimensional transducer array, the multi-dimensional transducer array comprising a quarter wavelength transducer with a dematching layer, the semiconductor chip electrically connected to the multi-dimensional transducer array through the dematching layer; and
   contact pads formed on the dematching layer for ground and signaling from the semiconductor chip to an ultrasound imaging system, the dematching layer providing signal routing from the contact pads to the semiconductor chip and from the semiconductor chip to the multi-dimensional transduce array.

14. The ultrasound transducer probe of claim 13, further comprising flexible circuit material connected by asperity contact to the contact pads.

15. The ultrasound transducer probe of claim 13 wherein transducer elements of the multi-dimensional transducer array connect to a first surface of the dematching layer, wherein the contact pads are formed on the first surface of the dematching layer, and wherein the semiconductor chip is flip-chip mounted to the dematching layer on a second surface opposite the first surface.

16. The ultrasound transducer probe of claim 13, wherein first kerfs separate elements of the multi-dimensional transducer array and extend through the dematching layer and wherein second kerfs form the contact pads and extend through the dematching layer, the first and second kerfs separating parts of the dematching layer for the signal routing.

17. The ultrasound transducer probe of claim 13, wherein a first one of the contact pads is a ground connection pad where the dematching layer connects the ground connection pad to elements of the multi-dimensional transducer array with a path separate from the semiconductor chip.

18. A method for connecting electronics with an array of acoustic elements, the method comprising:
   connecting an integrated circuit directly to a first surface of a dematching layer of the acoustic elements; and
   connecting conductors to a second surface of the dematching layer, the second surface opposite the first surface, the conductors connected to pads on the second surface outside of a footprint on the dematching layer of the acoustic elements.

19. The method of claim 18 wherein a portion of the dematching layer extends outside the footprint of the acoustic elements, wherein the integrated circuit extends along the first surface outside of the footprint, and wherein connecting the conductors comprises connecting traces on a flexible circuit to the portion of the dematching layer extending outside of the footprint.

20. The method of claim 18 wherein connecting the integrated circuit comprises connecting with flip-chip bonding and without an intervening layer.

\* \* \* \* \*